US006835564B1

(12) United States Patent
Donoho et al.

(10) Patent No.: US 6,835,564 B1
(45) Date of Patent: Dec. 28, 2004

(54) HUMAN ENDOTHELIN CONVERTING ENZYME-LIKE PROTEINS AND POLYNUCLEOTIDES ENCODING THE SAME

(75) Inventors: Gregory Donoho, The Woodlands, TX (US); C. Alexander Turner, Jr., The Woodlands, TX (US); Michael C. Nehls, Stockdorf (DE); Glenn Friedrich, Houston, TX (US); Brian Zambrowicz, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 36 days.

(21) Appl. No.: 10/305,413

(22) Filed: Nov. 25, 2002

Related U.S. Application Data

(63) Continuation of application No. 09/667,373, filed on Sep. 22, 2000, now Pat. No. 6,524,840.
(60) Provisional application No. 60/176,689, filed on Jan. 18, 2000, and provisional application No. 60/156,102, filed on Sep. 24, 1999.

(51) Int. Cl.[7] .............................. C12N 9/48; C07K 1/00

(52) U.S. Cl. ....................... 435/212; 435/183; 530/350; 536/23.1; 536/23.2

(58) Field of Search ................................ 435/212, 183; 530/350, 23.1, 23.2

(56) References Cited

U.S. PATENT DOCUMENTS

| | | | |
|---|---|---|---|
| 4,215,051 A | 7/1980 | Schroeder et al. | 260/346.7 |
| 4,376,110 A | 3/1983 | David et al. | 430/513 |
| 4,946,778 A | 8/1990 | Ladner et al. | 435/69.6 |
| 5,338,726 A | 8/1994 | Shiosaki et al. | 514/19 |
| 5,462,869 A | 10/1995 | Ohwaki et al. | 435/212 |
| 5,688,640 A | 11/1997 | Yanagisawa | 435/6 |
| 5,736,376 A | 4/1998 | Yanagisawa | 435/212 |
| 5,736,736 A | 4/1998 | Dickson et al. | 250/227.11 |
| 5,837,458 A | 11/1998 | Minshull et al. | 435/6 |
| 5,869,336 A | 2/1999 | Meyer et al. | 435/348 |
| 5,877,397 A | 3/1999 | Lonberg et al. | 800/2 |
| 6,075,181 A | 6/2000 | Kucherlapati et al. | 800/25 |

FOREIGN PATENT DOCUMENTS

| | | |
|---|---|---|
| WO | WO 95 14095 A | 5/1995 |
| WO | WO 99 38972 A | 8/1999 |

OTHER PUBLICATIONS

Bird et al, 1988, "Single–Chain Antigen–Binding Proteins", Science 242:423–426.

Bilter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Greenspan et al, 1993, "Idiotypes: structure and immunogenicity", FASEB Journal 7:437–444.

Huse et al, 1989, "Generation of a Large Combinatorial Library of the Immunoglobulin Reperoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci, USA 85:5879–5883.

Inoue et al. 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides". Nucleic Acids Research 15(15):6131–6149.

Inouye & Inouye, 1985, "Up–promoter mutations in the Ipp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS USA 88:8972–8976.

Kohler & Milstein, 1975, "Continuous cultures of fused cells secreting antibody of predefined specificity", Nature 256:495–497.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg. 1981, "Selection for animal cells that express the *Escherichia coli* gene coding for xanthine–guanine phosphoribosyltransferase", Proc. Natl. Acad. Sci. USA 78(74):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

(List continued on next page.)

*Primary Examiner*—Richard Hutson

(57) ABSTRACT

Novel human polynucleotide and polypeptide sequences are disclosed that can be used in therapeutic, diagnostic, and pharmacogenomic applications.

1 Claim, No Drawings

OTHER PUBLICATIONS

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations within the Polyhedrin Gene"; J. Virol. 46(2):584–583.

Stein et al. 1988. "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Meidated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthesis in *Escherichia coli*", J. Biol. Chemistry 264(10):5503–5509.

Ward et al, 1989, "Binding activities of a repertoire of single immunoglobulin variable domains secreted *Escherichia coli*", Nature 341:544–546.

Wigler et al, 1980, "Transformation of mammalian cells with an amplifable dominant–acting gene", Proc. Natl. Acad. Sci. USA 77(6):3067–3570.

Emoto, N. and Yanagisawa, M., 1995, Endothelin–converting Enzyme–2 is a Membrane–bound, Phosphoramidon–sensitive Metalloprotease with Acidic pH Optimum, Journal of Biological Chemistry 270(25):15262–15268.

EMBL Database, Heidelberg, FRG E,est_Hum17 accession No. BE793958 Sep. 21, 2000 NIH–MGC: 601586946F1 NID_MGC_7 Homo sapiens cDNA clone Image: 39411465', mRNA sequence: XP002161978.

Cote et al., 1983, "Generation of human monoclonal antibodies reactive with cellular antigens," Proc. Natl. Acad. Sci. USA 80:2026–2030.

Wigler et al, 1977, "Transfer of Purified Herpes Virus Thymidine Kinase Gene to Cultured Mouse Cells", Cell 11:223–232.

SEQUENCE LISTING

<160> NUMBER OF SEQ ID NOS: 5

<210> SEQ ID NO 1
<211> LENGTH: 765
<212> TYPE: DNA
<213> ORGANISM: homo sapiens

<400> SEQUENCE: 1

```
atggcctctc caggggcagg tagggcgcct ccggagttac cggagcggaa ctgcgggtac      60
cgcgaagtcg agtactggga tcagcgctac caaggcgcag ccgattctgc cccctacgat     120
tggttcgggg acttctcctc cttccgtgcc ctcctagagc cggagctgcg gcccgaggac     180
cgtatccttg tgctaggttg cgggaacagt gccctgagct acgagctgtt cctcggaggc     240
ttccctaatg tgaccagtgt ggactactca tcagtcgtgg tggctgccat gcaggctcgc     300
tatgcccatg tgccgcagct gcgctgggag accatggatg tgcggaagct ggacttcccc     360
agtgcttctt ttgatgtggt gctcgagaag ggcacgctgg atgccctgct ggctggggaa     420
cgagatccct ggaccgtgtc ctctgaaggt gtccacactg tggaccaggt gttgagtgag     480
gtgagccgcg tgcttgtccc tggaggccgg tttatctcaa tgacttctgc tgcccccac      540 tttcggacca gacactatgc ccaagcctat tatggctggt ccctgaggca tgctacctat     600
ggcagcggtt tccacttcca tctctacctc atgcacaagg gcgggaagct cagtgtggcc     660
cagctggctc tgggggccca aatcctctca cccccagac ctcccacctc accttgcttc      720
cttcaggact cagatcatga ggacttcctt agtgccattc agctc                     765
```

<210> SEQ ID NO 2
<211> LENGTH: 255
<212> TYPE: PRT
<213> ORGANISM: homo sapiens

<400> SEQUENCE: 2

```
Met Ala Ser Pro Gly Ala Gly Arg Ala Pro Pro Glu Leu Pro Glu Arg
 1               5                  10                  15

Asn Cys Gly Tyr Arg Glu Val Glu Tyr Trp Asp Gln Arg Tyr Gln Gly
             20                  25                  30

Ala Ala Asp Ser Ala Pro Tyr Asp Trp Phe Gly Asp Phe Ser Ser Phe
         35                  40                  45
```

-continued

```
Arg Ala Leu Leu Glu Pro Glu Leu Arg Pro Glu Asp Arg Ile Leu Val
    50                  55                  60
Leu Gly Cys Gly Asn Ser Ala Leu Ser Tyr Glu Leu Phe Leu Gly Gly
65                  70                  75                  80
Phe Pro Asn Val Thr Ser Val Asp Tyr Ser Ser Val Val Val Ala Ala
                85                  90                  95
Met Gln Ala Arg Tyr Ala His Val Pro Gln Leu Arg Trp Glu Thr Met
            100                 105                 110
Asp Val Arg Lys Leu Asp Phe Pro Ser Ala Ser Phe Asp Val Val Leu
            115                 120                 125
Glu Lys Gly Thr Leu Asp Ala Leu Leu Ala Gly Glu Arg Asp Pro Trp
        130                 135                 140
Thr Val Ser Ser Glu Gly Val His Thr Val Asp Gln Val Leu Ser Glu
145                 150                 155                 160
Val Ser Arg Val Leu Val Pro Gly Gly Arg Phe Ile Ser Met Thr Ser
                165                 170                 175
Ala Ala Pro His Phe Arg Thr Arg His Tyr Ala Gln Ala Tyr Tyr Gly
            180                 185                 190
Trp Ser Leu Arg His Ala Thr Tyr Gly Ser Gly Phe His Phe His Leu
            195                 200                 205
Tyr Leu Met His Lys Gly Gly Lys Leu Ser Val Ala Gln Leu Ala Leu
        210                 215                 220
Gly Ala Gln Ile Leu Ser Pro Pro Arg Pro Pro Thr Ser Pro Cys Phe
225                 230                 235                 240
Leu Gln Asp Ser Asp His Glu Asp Phe Leu Ser Ala Ile Gln Leu
                245                 250                 255

<210> SEQ ID NO 3
<211> LENGTH: 2652
<212> TYPE: DNA
<213> ORGANISM: homo sapiens

<400> SEQUENCE: 3
atggcctctc caggggcagg tagggcgcct ccggagttac cggagcggaa ctgcgggtac      60
cgcgaagtcg agtactggga tcagcgctac caaggcgcag ccgattctgc cccctacgat     120
tggttcgggg acttctcctc cttccgtgcc ctcctagagc cggagctgcg gcccgaggac     180
cgtatccttg tgctaggttg cgggaacagt gccctgagct acgagctgtt cctcggaggc     240
ttccctaatg tgaccagtgt ggactactca tcagtcgtgg tggctgccat gcaggctcgc     300
tatgcccatg tgccgcagct gcgctgggag accatggatg tgcggaagct ggacttcccc     360
agtgcttctt ttgatgtggt gctcgagaag ggcacgctgg atgccctgct ggctggggaa     420
cgagatccct ggaccgtgtc ctctgaaggt gtccacactg tggaccaggt gttgagtgag     480
gtgggattcc agaaggggac aagacagctg ttaggctcac gcacgcagct ggagctggtc     540
ttagcaggtg cctctctact gctggctgca ctgcttctgg gctgccttgt ggccctaggg     600
gtccagtacc acagagaccc atcccacagc acctgcctta cagaggcctg cattcgagtg     660
gctggaaaaa tcctggagtc cctggaccga ggggtgagcc cctgtgagga cttttaccag     720
ttctcctgtg ggggctggat tcggaggaac ccctgcccg atgggcgttc tgctggaac      780 accttcaaca gcctctggga ccaaaaccag gccatactga agcacctgct tgaaaacacc     840
accttcaact ccagcagtga agctgagcag aagacacagc gcttctacct atcttgccta     900
caggtggagc gcattgagga gctgggagcc cagccactga gagacctcat tgagaagatt     960
```

-continued

```
ggtggttgga acattacggg gccctgggac caggacaact ttatggaggt gttgaaggca    1020
gtagcaggga cctacagggc cacccccattc ttcaccgtct acatcagtgc tgactctaag    1080
agttccaaca gcaatgttat ccaggtggac cagtctgggc tctttctgcc ctctcgggat    1140
tactacttaa acagaactgc caatgagaaa gtgctcactg cctatctgga ttacatggag    1200
gaactgggga tgctgctggg tgggcggccc acctccacga gggagcagat gcagcaggtg    1260
ctggagttgg agatacagct ggccaacatc acagtgcccc aggaccagcg gcgcgacgag    1320
gagaagatct accacaagat gagcatttcg gagctgcagg ctctggcgcc ctccatggac    1380
tggcttgagt tcctgtcttt cttgctgtca ccattggagt tgagtgactc tgagcctgtg    1440
gtggtgtatg ggatggatta tttgcagcag gtgtcagagc tcatcaaccg cacggaacca    1500
agcatcctga acaattacct gatctggaac ctggtgcaaa agacaacctc aagcctggac    1560
cgacgctttg agtctgcaca agagaagctg ctggagaccc tctatggcac taagaagtcc    1620
tgtgtgccga ggtggcagac ctgcatctcc aacacggatg acgcccttgg ctttgctttg    1680
gggtccctct tcgtgaaggc cacgtttgac cggcaaagca agaaattgc agaggggatg    1740 atcagcgaaa tccggaccgc atttgaggag gccctgggac agctggtttg gatgatgag    1800 aagacccgcc aggcagccaa ggagaaagca gatgccatct atgatatgat tggtttccca    1860
gactttatcc tggagcccaa agagctggat gatgtttatg acgggtacga aatttctgaa    1920
gattctttct tccaaaacat gttgaatttg tacaacttct ctgccaaggt tatggctgac    1980
cagctccgca agcctcccag ccgagaccag tggagcatga cccccagac agtgaatgcc    2040 tactaccttc caactaagaa tgagatcgtc ttccccgctg gcatcctgca ggccccttc    2100 tatgcccgca accaccccaa ggccctgaac ttcgtggca tcgtgtggt catgggccat    2160 gagttgacgc atgcctttga tgaccaaggg gcgcgagtatg acaaagaagg gaacctgcgg    2220
ccctggtggc agaatgagtc cctggcagcc ttccggaacc acacggcctg catggaggaa    2280
cagtacaatc aataccaggt caatggggag aggctcaacg gccgccagac gctgggggag    2340
aacattgctg acaacggggg gctgaaggct gcctacaatg cttacaaagc atggctgaga    2400
aagcatgggg aggagcagca actgccagcc gtgggctca ccaaccacca gtcttcttc    2460 gtgggatttg cccaggtgtg gtgctcggtc cgcacaccag agagctctca cgaggggctg    2520
gtgaccgacc cccacagccc tgcccgcttc cgcgtgctgg gcactctctc caactcccgt    2580
gacttcctgc ggcacttcgg ctgccctgtc ggctccccca tgaacccagg gcagctgtgt    2640
gaggtgtggt ag                                                        2652
```

<210> SEQ ID NO 4
<211> LENGTH: 883
<212> TYPE: PRT
<213> ORGANISM: homo sapiens

<400> SEQUENCE: 4

```
Met Ala Ser Pro Gly Ala Gly Arg Ala Pro Pro Glu Leu Pro Glu Arg
  1               5                  10                  15

Asn Cys Gly Tyr Arg Glu Val Glu Tyr Trp Asp Gln Arg Tyr Gln Gly
                 20                  25                  30

Ala Ala Asp Ser Ala Pro Tyr Asp Trp Phe Gly Asp Phe Ser Ser Phe
             35                  40                  45

Arg Ala Leu Leu Glu Pro Glu Leu Arg Pro Glu Asp Arg Ile Leu Val
         50                  55                  60
```

-continued

```
Leu Gly Cys Gly Asn Ser Ala Leu Ser Tyr Glu Leu Phe Leu Gly Gly
 65                  70                  75                  80

Phe Pro Asn Val Thr Ser Val Asp Tyr Ser Val Val Ala Ala
                 85                  90                  95

Met Gln Ala Arg Tyr Ala His Val Pro Gln Leu Arg Trp Glu Thr Met
                100                 105                 110

Asp Val Arg Lys Leu Asp Phe Pro Ser Ala Ser Phe Asp Val Val Leu
                115                 120                 125

Glu Lys Gly Thr Leu Asp Ala Leu Leu Ala Gly Arg Asp Pro Trp
        130                 135                 140

Thr Val Ser Ser Glu Gly Val His Thr Val Asp Gln Val Leu Ser Glu
145                 150                 155                 160

Val Gly Phe Gln Lys Gly Thr Arg Gln Leu Leu Gly Ser Arg Thr Gln
                165                 170                 175

Leu Glu Leu Val Leu Ala Gly Ala Ser Leu Leu Leu Ala Ala Leu Leu
                180                 185                 190

Leu Gly Cys Leu Val Ala Leu Gly Val Gln Tyr His Arg Asp Pro Ser
            195                 200                 205

His Ser Thr Cys Leu Thr Glu Ala Cys Ile Arg Val Ala Gly Lys Ile
        210                 215                 220

Leu Glu Ser Leu Asp Arg Gly Val Ser Pro Cys Glu Asp Phe Tyr Gln
225                 230                 235                 240

Phe Ser Cys Gly Gly Trp Ile Arg Arg Asn Pro Leu Pro Asp Gly Arg
                245                 250                 255

Ser Arg Trp Asn Thr Phe Asn Ser Leu Trp Asp Gln Asn Gln Ala Ile
                260                 265                 270

Leu Lys His Leu Leu Glu Asn Thr Thr Phe Asn Ser Ser Glu Ala
        275                 280                 285

Glu Gln Lys Thr Gln Arg Phe Tyr Leu Ser Cys Leu Gln Val Glu Arg
        290                 295                 300

Ile Glu Glu Leu Gly Ala Gln Pro Leu Arg Asp Leu Ile Glu Lys Ile
305                 310                 315                 320

Gly Gly Trp Asn Ile Thr Gly Pro Trp Asp Gln Asp Asn Phe Met Glu
                325                 330                 335

Val Leu Lys Ala Val Ala Gly Thr Tyr Arg Ala Thr Pro Phe Phe Thr
                340                 345                 350

Val Tyr Ile Ser Ala Asp Ser Lys Ser Ser Asn Ser Asn Val Ile Gln
            355                 360                 365

Val Asp Gln Ser Gly Leu Phe Leu Pro Ser Arg Asp Tyr Tyr Leu Asn
        370                 375                 380

Arg Thr Ala Asn Glu Lys Val Leu Thr Ala Tyr Leu Asp Tyr Met Glu
385                 390                 395                 400

Glu Leu Gly Met Leu Leu Gly Gly Arg Pro Thr Ser Thr Arg Glu Gln
                405                 410                 415

Met Gln Gln Val Leu Glu Leu Glu Ile Gln Leu Ala Asn Ile Thr Val
                420                 425                 430

Pro Gln Asp Gln Arg Arg Asp Glu Lys Ile Tyr His Lys Met Ser
            435                 440                 445

Ile Ser Glu Leu Gln Ala Leu Ala Pro Ser Met Asp Trp Leu Glu Phe
        450                 455                 460

Leu Ser Phe Leu Leu Ser Pro Leu Glu Leu Ser Asp Ser Glu Pro Val
465                 470                 475                 480

Val Val Tyr Gly Met Asp Tyr Leu Gln Gln Val Ser Glu Leu Ile Asn
```

-continued

```
                    485                 490                 495
Arg Thr Glu Pro Ser Ile Leu Asn Asn Tyr Leu Ile Trp Asn Leu Val
                500                 505                 510
Gln Lys Thr Thr Ser Ser Leu Asp Arg Arg Phe Glu Ser Ala Gln Glu
            515                 520                 525
Lys Leu Leu Glu Thr Leu Tyr Gly Thr Lys Lys Ser Cys Val Pro Arg
        530                 535                 540
Trp Gln Thr Cys Ile Ser Asn Thr Asp Asp Ala Leu Gly Phe Ala Leu
545                 550                 555                 560
Gly Ser Leu Phe Val Lys Ala Thr Phe Asp Arg Gln Ser Lys Glu Ile
                565                 570                 575
Ala Glu Gly Met Ile Ser Glu Ile Arg Thr Ala Phe Glu Glu Ala Leu
            580                 585                 590
Gly Gln Leu Val Trp Met Asp Glu Lys Thr Arg Gln Ala Ala Lys Glu
        595                 600                 605
Lys Ala Asp Ala Ile Tyr Asp Met Ile Gly Phe Pro Asp Phe Ile Leu
    610                 615                 620
Glu Pro Lys Glu Leu Asp Asp Val Tyr Asp Gly Tyr Glu Ile Ser Glu
625                 630                 635                 640
Asp Ser Phe Phe Gln Asn Met Leu Asn Leu Tyr Asn Phe Ser Ala Lys
                645                 650                 655
Val Met Ala Asp Gln Leu Arg Lys Pro Pro Ser Arg Asp Gln Trp Ser
            660                 665                 670
Met Thr Pro Gln Thr Val Asn Ala Tyr Tyr Leu Pro Thr Lys Asn Glu
        675                 680                 685
Ile Val Phe Pro Ala Gly Ile Leu Gln Ala Pro Phe Tyr Ala Arg Asn
    690                 695                 700
His Pro Lys Ala Leu Asn Phe Gly Gly Ile Gly Val Val Met Gly His
705                 710                 715                 720
Glu Leu Thr His Ala Phe Asp Asp Gln Gly Arg Glu Tyr Asp Lys Glu
                725                 730                 735
Gly Asn Leu Arg Pro Trp Trp Gln Asn Glu Ser Leu Ala Ala Phe Arg
            740                 745                 750
Asn His Thr Ala Cys Met Glu Glu Gln Tyr Asn Gln Tyr Gln Val Asn
        755                 760                 765
Gly Glu Arg Leu Asn Gly Arg Gln Thr Leu Gly Glu Asn Ile Ala Asp
    770                 775                 780
Asn Gly Gly Leu Lys Ala Ala Tyr Asn Ala Tyr Lys Ala Trp Leu Arg
785                 790                 795                 800
Lys His Gly Glu Glu Gln Gln Leu Pro Ala Val Gly Leu Thr Asn His
                805                 810                 815
Gln Leu Phe Phe Val Gly Phe Ala Gln Val Trp Cys Ser Val Arg Thr
            820                 825                 830
Pro Glu Ser Ser His Glu Gly Leu Val Thr Asp Pro His Ser Pro Ala
        835                 840                 845
Arg Phe Arg Val Leu Gly Thr Leu Ser Asn Ser Arg Asp Phe Leu Arg
    850                 855                 860
His Phe Gly Cys Pro Val Gly Ser Pro Met Asn Pro Gly Gln Leu Cys
865                 870                 875                 880
Glu Val Trp

<210> SEQ ID NO 5
<211> LENGTH: 985
```

```
<212> TYPE: DNA
<213> ORGANISM: homo sapiens

<400> SEQUENCE:

ggctctggct gcccggcggt tgagagcatg gcctctccag gggcaggtag ggcgcctccg      60
gagttaccgg agcggaactg cgggtaccgc gaagtcgagt actgggatca gcgctaccaa     120
ggcgcagccg attctgcccc ctacgattgg ttcggggact tctcctcctt ccgtgccctc     180
ctagagccgg agctgcggcc cgaggaccgt atccttgtgc taggttgcgg gaacagtgcc     240
ctgagctacg agctgttcct cggaggcttc cctaatgtga ccagtgtgga ctactcatca     300
gtcgtggtgg ctgccatgca ggctcgctat gcccatgtgc cgcagctgcg ctgggagacc     360
atggatgtgc ggaagctgga cttccccagt gcttcttttg atgtggtgct cgagaagggc     420
acgctggatg ccctgctggc tggggaacga gatccctgga ccgtgtcctc tgaaggtgtc     480
cacactgtgg accaggtgtt gagtgaggtg agccgcgtgc ttgtccctgg aggccggttt     540
atctcaatga cttctgctgc cccccacttt cggaccagac actatgccca agcctattat     600
ggctggtccc tgaggcatgc tacctatggc agcggtttcc acttccatct ctacctcatg     660
cacaagggcg ggaagctcag tgtggcccag ctggctctgg gggcccaaat cctctcaccc     720
cccagacctc ccacctcacc ttgcttcctt caggactcag atcatgagga cttccttagt     780
gccattcagc tctgaggcca gagcatggtc ctccacccct cctgccattc tgccctgggc     840
tcctcaggta gttggaattc ctgacttagg acttggggtt gggtccaagg tgcttacatc     900 ccagggcct catgcctaag atagagggtg ggagcgaacc cacatgaacc aatacagccc     960
agctccaact aaaaaaaaaa aaaaa                                           985
```

HUMAN ENDOTHELIN CONVERTING ENZYME-LIKE PROTEINS AND POLYNUCLEOTIDES ENCODING THE SAME

The present application claims priority to U.S. Provisional Applications No. 60/156,102 and 60/176,689 which were filed on Sep. 24, 1999 and Jan. 18, 2000 and a continuation of 09/667,373, filed Sep. 22, 2000 now U.S. Pat. No. 6,524,840 respectively, and are herein incorporated by reference in their entirety.

1. INTRODUCTION

The present invention relates to the discovery, identification, and characterization of novel human polynucleotides encoding proteins that share sequence similarity with mammalian endothelin converting enzymes. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring, and the treatment of physiological disorders.

2. BACKGROUND OF THE INVENTION

Endothelin converting enzymes cleave endothelin precursor protein to its biologically active product. Given the strong vasoconstrictive activity of endothelins and their importance in, for example, renal and cardiovascular pathogenesis, methods of modulating endothelin production and activity have been subject to significant scientific scrutiny.

3. SUMMARY OF THE INVENTION

The present invention relates to the discovery, identification, and characterization of nucleotides that encode novel human proteins, and the corresponding amino acid sequences of these proteins. The novel human proteins (NHPs) novel human proteins, and the corresponding amino acid sequences of these proteins. The novel human proteins (NHPs) described for the first time herein share structural similarity with animal endothelin converting enzymes. As such, the NHPs may be involved in regulating (i.e., directly or indirectly activating or inhibiting) endothelin activity in human cells and/or tissues. The described NHPs represent a new protein having a range of homologs and orthologs from a variety of species and phyla.

The novel human nucleic acid sequences described herein, encode proteins/open reading frames (ORF) of 255 and 883 amino acids in length (see SEQ ID NOS: 2 and 4).

The invention also encompasses agonists and antagonists of the described NHPs, including small molecules, large molecules, mutant NHPs, or portions thereof that compete with native NHPs, NHP peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotides (e.g., expression constructs that place the described gene under the control of a strong promoter system), and transgenic animals that express a NHP transgene, or "knock-outs" (which can be conditional) that do not express a functional NHP.

Further, the present invention also relates to processes for identifying compounds that modulate, i.e., act as agonists or antagonists, of NHP expression and/or NHP product activity that utilize purified preparations of the described NHP and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the described endothelin converting enzyme-like ORFs that encode the described NHP amino acid sequences. SEQ ID NO: 5 describes the a NHP ORF (SEQ ID NO:1) with flanking sequences.

5. DETAILED DESCRIPTION OF THE INVENTION

The NHPs, described for the first time herein, are novel proteins that are expressed in, inter alia, human cell lines, and fetal brain, cerebellum, thymus, spleen, lymph node, bone marrow, trachea, kidney, liver, prostate, testis, thyroid, adrenal gland, pancreas, salivary gland, stomach, small intestine, colon, muscle, adipose, esophagus, bladder, cervix, rectum, and pericardium cells. The described sequences were compiled from gene trapped cDNAs and clones isolated from a human liver cDNA library (Edge Biosystems, Gaithersburg, Md.), as well as published sequences that did not represent or identify regions of the presently described proteins. Given the important physiological role of endothelin, endothelin converting enzymes have been subject to considerable scrutiny as described in U.S. Pat. Nos. 5,736,376, 5,688,640 (describing recombinant expression and screening assays), U.S. Pat. No. 5,338,726 (describing inhibitors), and U.S. Pat. No. 5,462,869 (describing general methods of purifying such proteins), all of which are hereby incorporated by reference in their entirety.

The present invention encompasses the nucleotides presented in the Sequence Listing, host cells expressing such nucleotides, the expression products of such nucleotides, and: (a) nucleotides that encode mammalian homologs of the described genes, including the specifically described NHP, and the NHP related products; (b) nucleotides that encode one or more portions of a NHP that correspond to functional domains, and the polypeptide products specified by such nucleotide sequences, including but not limited to the novel regions of any active domain(s); (c) isolated nucleotides that encode mutant versions, engineered or naturally occurring, of a NHP in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458, herein incorporated by reference). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of SEQ ID NO:1 (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. The oligonucleotides, typically between about 16 to about 40 (or any whole number within the stated range) nucleotides in length may partially overlap each other and/or the NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethyl-aminomethyl-2-thiouridine, 5-carboxymethylamino-methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences present within the NHP product disclosed herein. The template for the reaction may be total RNA, mRNA, and/or cDNA obtained by reverse transcription of mRNA prepared from, for example, human or non-human cell lines or tissue, such as prostate, rectum, colon, or adrenal gland, known or suspected to express an allele of a NHP gene. The PCR product can be subcloned and sequenced to ensure that the amplified sequences represent the sequence of the desired NHP gene. The PCR fragment can then be used to isolate a full length CDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, etc.), or a CDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, regulatable, viral (particularly retroviral LTR promoters) the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The described NHP or NHP peptides, NHP fusion proteins, NHP nucleotide sequences, antibodies, antagonists and agonists can be used in the detection of mutant NHPs or inappropriately expressed NHP for the diagnosis of disease. The NHP or NHP peptides, NHP fusion proteins, NHP nucleotide sequences, host cell expression systems, antibodies, antagonists, agonists and genetically engineered cells and animals can also be used for screening for drugs (or high throughput screening of combinatorial libraries) effective in the treatment of the symptomatic or phenotypic manifestations of perturbing the normal function of NHP in the body. The use of engineered host cells and/or animals can offer an advantage in that such systems allow not only for the identification of compounds that bind to the endogenous receptor for an NHP, but can also identify compounds that trigger NHP-mediated pathways.

Finally, the NHP products can be used as therapeutics. For example, soluble derivatives such as NHP peptides/domains corresponding to the NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate signal transduction which may act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHP, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences (SEQ ID NOS: 1 and 3) and the corresponding deduced amino acid sequence (SEQ ID NOS: 2 and 4) of the described NHPs are presented in the Sequence Listing. The NHP genes were obtained from a human liver cDNA library using probes and/or primers generated from human gene trapped sequence tags. Expression analysis has provided evidence that the described NHPs can be expressed in a wide range of human tissues as well as gene trapped human cells. SEQ ID NO:3 describes a full length ORF with flanking 5' and 3' sequences.

5.2 NHP Polypeptides

The described NHPs, NHP polypeptides, NHP peptide fragments, mutated, truncated, or deleted forms of the NHPs, and/or NHP fusion proteins can be prepared for a variety of uses. These uses include but are not limited to the generation of antibodies, as reagents in diagnostic assays, for the identification of other cellular gene products related to a NHP, as reagents in assays for screening for compounds that can be as pharmaceutical reagents useful in the therapeutic treatment of mental, biological, or medical disorders and disease.

The Sequence Listing discloses the amino acid sequence encoded by the described NHP genes. The NHPs each display a initiator methionine in a DNA sequence context consistent with a translation initiation sites, and have structural features characteristic of related endothelin converting proteins.

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, NY, herein incorporated by reference) are generically representative of all the various permutations and combinations of nucleic acid sequences that can encode such amino acid sequences.

The invention also encompasses proteins that are functionally equivalent to a NHP encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays. Where, as in the present instance, the NHP peptide or polypeptide is thought to be a membrane protein, expression systems can be engineered that produce soluble derivatives of a NHP (corresponding to a NHP extracellular and/or intracellular domains, or truncated polypeptides lacking one or more transmembrane domains) and/or NHP fusion protein products (especially NHP-Ig fusion proteins, i.e., fusions of a NHP domain, e.g., ECD, ΔTM to an IgFc), NHP antibodies and anti-idiotypic antibodies (including Fab fragments) which can be used in therapeutic applications. Preferably, the above expression systems are engineered to allow the desired peptide or polypeptide to be recovered from the culture media.

The expression systems that can be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited to, the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP gene coding sequence may be cloned individually into non-essential regions (for example the polyhedrin gene) of the virus and placed under control of an AcNPV promoter (for example the polyhedrin promoter). Successful insertion of NHP gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells can be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines can be particularly useful in screening and evaluation of compounds that affect the endogenous activity of the NHP product.

A number of selection systems can be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$. nitriloacetic acid-agarose columns and histidine-tagged proteins are selectively eluted with imidazole-containing buffers.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, a NHP peptide (e.g., one corresponding to a functional domain of a NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxoid or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mabs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or fragments of such anti-idiotypes can be used in therapeutic regimens involving a NHP signaling pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All patents, patent applications, and publications cited herein are incorporated by reference in their entirety.

What is claimed is:

1. A substantially isolated polypeptide comprising the amino acid sequence of SEQ ID NO: 2.

\* \* \* \* \*